United States Patent [19]

Sunshine et al.

[11] Patent Number: 4,927,854

[45] Date of Patent: May 22, 1990

[54] SUSTAINED/ENHANCED ANALGESIA

[75] Inventors: Abraham Sunshine, New York; Eugene M. Laska, Larchmont, both of N.Y.

[73] Assignee: Analgesic Associates, Larchmont, N.Y.

[21] Appl. No.: 384,101

[22] Filed: Jul. 21, 1989

Related U.S. Application Data

[63] Continuation of Ser. No. 137,866, Dec. 24, 1987, abandoned.

[51] Int. Cl.$^5$ .............................................. A61K 31/19
[52] U.S. Cl. .................................... 514/570; 514/557; 514/568; 514/947; 514/960; 514/962
[58] Field of Search ............... 514/557, 568, 570, 960, 514/947, 962

[56] References Cited

U.S. PATENT DOCUMENTS

| | | |
|---|---|---|
| 3,637,767 | 1/1972 | Alvarez . |
| 3,755,427 | 8/1973 | Adams et al. . |
| 4,439,451 | 3/1984 | Coleman ............................. 514/570 |
| 4,440,787 | 4/1984 | de Vincentiis . |
| 4,443,476 | 4/1984 | Lomen ............................... 514/570 |
| 4,486,436 | 12/1984 | Sunshine et al. . |
| 4,489,080 | 12/1984 | Lomen ............................... 514/570 |
| 4,501,727 | 2/1985 | Armitage et al. . |
| 4,552,899 | 11/1985 | Sunshine et al. . |
| 4,567,183 | 1/1986 | Sunshine et al. . |
| 4,619,934 | 10/1986 | Sunshine et al. . |
| 4,722,938 | 2/1988 | Sunshine et al. . |

FOREIGN PATENT DOCUMENTS 0205215 12/1986 European Pat. Off. .

OTHER PUBLICATIONS

"The Metabolic Chiral Inversion of 2-Arylpropionic Acids-A Novel Route with Pharmacological Consequences", *J. Pharm. Pharmaco.*, Andrew J. Hutt et al., vol. 35 (1983), pp. 693-704.

"Naproxen", *Anti-Inflammatory and Anti-Rheumatic Drugs*, Anthony C. Allison et al., vol. 11, Chapter 9, Ed.: K. D. Rainsford, CRC Press, Inc., Boca Raton, Fla. (1985), p. 172.

"The Importance of Stereochemistry in the Clinical Pharmocokinetics of the 2-Arylpropionic Acid Non-Steroidal Anti-Inflammatory Drugs", *Clinical Pharmacokinetics*, Andrew J. Hutt et al., vol. 9 (1984), pp. 371-373.

"Anatagonism of Slow Reacting Substance in Anaphylaxis (SRS-A) and Other Spasmogens on the Guinea Pig Trachial Chain by Hydratropic Acids and Their Effects on Anaphylaxis", *Journal of Medicinal Chemistry*, Margaret E. Greig et al., vol. 18, No. 1 (1975), pp. 112-116.

"Flurbiprofen, A New Potent Inhibitor of Platelet Aggregation", *Thrombosis Research*, E. E. Nishizawa et al., vol. 3, No. 5 (1973), pp. 577-588.

"Stoichiometry and Kinetics of the Interaction of Prostaglandin H Synthase with Anti-Inflammatory Agents", *The Journal of Biological Chemistry*, Richard J. Kulmacz et al., vol. 260, No. 23 (Oct. 15, 1985), pp. 12572-12578.

"The Resolution of Enantiomeric Drugs Using HPLC Chiral Stationary Phases", *Pharm. Technol.*, T. D. Doyle et al., vol. 9, No. 2 (1985), pp. 28-32.

"Application of High-Performance Liquid Chromatographic Chiral Stationary Phases to Pharmaceutical Analysis: Structural and Conformational Effects in the Direct Enantiomeric Resolution of Alpha Methylarylacetic Acid Antiinflammatory Agents", *J. Chromatogr.*, I. W. Wainer et al., vol. 284, No. I (1984), pp. 117-124.

"Enantiospecific High-Performance Liquid Chromatographic Analysis of 2-Phenylpropionic Acid, Ketoprofen and Fenoprofen", *Journal of Chromatography*, B. C. Sallustio et al., vol. 374 (1986), pp. 329-337.

"Gas Chromatographic Separation of Optically Active Anti-Inflammatory 2-Arylapropionic Acids Using (+)- or (−)-Amphetamine as Derivatizing Reagent", *J. Chromatogr. Biomed. Appl.*, N. N. Singh et al., vol. 378, No. 1 (1986), pp. 125-135.

"Isomeric Inversion of Ibuprofen (R)-Enantiomer in Humans", *Journal of Pharmaceutical Sciences*, D. G. Kaiser et al., vol. 65, No. 2, Feb. 1976, pp. 269-273.

Correspondence relating to study undertaken by Dr. Sunshine at the request of the Boots Company Ltd., 1982-1986.

*Primary Examiner*—Jacqueline V. Howard
*Attorney, Agent, or Firm*—Burns, Doane, Swecker & Mathis

[57] ABSTRACT

Sustained and enhanced analgesic response is elicited in a mammalian organism in need of such treatment, i.e., a mammal suffering pain, by administering thereto a unit dosage sustainedly enhancing, analgesically effective amount of the free acid S(+) flurbiprofen enantiomer, said enantiomer being substantially free of its R(−) flurbiprofen antipode.

41 Claims, No Drawings

SUSTAINED/ENHANCED ANALGESIA

This application is a continuation of application Ser No. 137,866, filed Dec. 24, 1987, now abandoned.

CROSS-REFERENCE TO COMPANION APPLICATIONS

Our copending applications, Ser. No. 071,914, filed July 10, 1987, Ser. No. 121,848, filed Nov. 17, 1987, and Ser. No. 121,849, filed Nov. 17, 1987, all assigned to the assignee hereof.

BACKGROUND OF THE INVENTION

1. Field of the Invention

The present invention relates to the use of free acid S(+) flurbiprofen to elicit a sustained and enhanced analgesic response in mammalian organisms in need of such treatment, and to certain pharmaceutical compositions comprising unit dosage effective amounts of S(+) flurbiprofen.

2. Description of the Art

Flurbiprofen, also known as (±)-2-fluoro-α-methyl-[1,1'-biphenyl]-4-acetic acid, as (±)-2-fluoro-α-methyl-4-biphenylacetic acid or as (±)-2-(2-fluoro-4-biphenylyl)propionic acid, is described in U.S. Pat. No. 3,755,427 and has the structural formula:

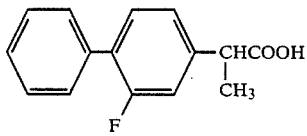

The compound is well-known as a nonsteroidal anti-inflammatory drug having analgesic and antipyretic activity. Flurbiprofen is not yet marketed in the United States, but has been on the market in numerous countries overseas, including Europe, for a number of years. Tradenames and codenames by which it is known include Ansaid, Cebutid, Froben, BTS 18322 and U-27182. As Froben, the drug is available abroad as tablets containing 50 or 100 mg of flurbiprofen. For rheumatic disorders such as rheumatoid arthritis, it is recommended at a daily dose of 150 to 200 mg in divided doses of two to four per day, increased to a daily dose of 300 mg in acute conditions. See Martindale, *The Extra Pharmacoooeia*, 28th edition, ed. James E. F. Reynolds, London, The Pharmaceutical Press, 1982, p. 255. As an analgesic, it is usually administered at the 50 mg dosage level every 4 to 6 hours, up to 300 mg per day. Flurbiprofen has been found useful in controlling acute and chronic pain, including that associated with ankylosing spondylitis, osteoarthritis, rheumatoid arthritis, postsurgical dental pain, postsurgical gynecological pain, postpartum uterine pain, primary dysmenorrhea, cancer pain, the pain of acute gout and the pain of acute bursitis/tendinitis of the shoulder. See *The American Journal of Medicine*, Proceedings of a Symposium, "Control of Acute and Chronic Pain with Ansaid (Flurbiprofen)", ed. Abraham Sunshine, M.D., Volume 80 (3A), Mar. 24, 1986.

As is apparent from its chemical nomenclature, flurbiprofen is a racemic mixture. It is only the racemic mixture which has in fact ever been marketed. There have, however, been a few isolated studies of the individual S(+) and R(−) isomers reported in the literature. These reflect that the S(+) enantiomer, analogously to other 2-arylpropionic acids, is the active form of flurbiprofen.

Hutt et al, *J. Pharm. Pharmacol.*, 35, 693–704 (1983), reviewed the earlier work on the metabolic chiral inversion of 2-arylpropionic acids, including ibuprofen, which they indicated was the first substituted 2-arylpropionic acid conclusively shown to undergo the inversion as well as the most studied member of the group. The authors noted that early workers found no significant difference in in vivo activity among the R(−) and S(+) isomers and the racemic mixture of ibuprofen in three different animal models, but very large differences in vitro between the R(−) and S(+) isomers, ascribing this discrepancy to the virtually quantitative conversion of the R(−) to the active S(+) isomer in vivo.

In the same paper, Hutt et al reported that, in contrast, for several other 2-arylpropionic acids, the inactive R(−) isomer was not converted in vivo to the active S(+) isomer as readily as ibuprofen, although the conversion seemed to occur to some extent over time. Naproxen, they noted, has been the only compound marketed as the S(+) enantiomer to date. Hutt et al concluded:

It is likely that benefits will be obtained from the use of the S(+)-enantiomer of 2-arylpropionates as drugs as opposed to the racemates. This is only found at present in the case of naproxen. In cases of rapid inversion, the inactive R(−) isomer serves merely as a prodrug for the active S(+)-antipode. Where inversion is slow, the R(−) enantiomer is an unnecessary impurity in the active S(+) form. Use of the S(+)-enantiomer would permit reduction of the dose given, remove variability in rate and extent of inversion as a source of variability in therapeutic response and would reduce any toxicity arising from non-stereospecific mechanisms.

Thus, in cases of rapid inversion, such as ibuprofen, where substantially equivalent in vivo responses have been reported for the individual enantiomers and the racemic drug, Hutt et al suggested that no benefits would be obtained from the use of the S(+) isomer because the inactive R(−) isomer merely acts as a prodrug for the active S(+) form. Contrariwise, in cases where chiral inversion is slow, e.g. naproxen, the use of the S(+) enantiomer is desirable for the several reasons enumerated by Hutt et al. Indeed, naproxen has been reported to be marketed as the d-isomer for one of the reasons given by Hutt et al, i.e. to reduce side effects (Allison et al, "Naproxen," Chapter 9 in *Anti-inflammatory and Anti-Rheumatic Drugs*, eds. Rainsford and Path, CRC Press Inc., Boca Raton, Fla., 1985, p. 172). However, the 1983 Hutt et al review is silent as to the possibility of chiral inversion in the case of flurbiprofen.

Another general report on earlier work has been provided by Hutt et al in *Clinical Pharmacokinetics*, 9, 371–373 (1984). In this article on the importance of stereochemical considerations in the clinical pharmacokinetics of 2-arylpropionic acids, the authors tabulated relative potencies of the enantiomers of a number of 2-arylpropionic acids in vivo and in vitro. The in vitro results showed the S or (+) isomer in each case to be the more active species. In vivo, however, the results were not consistent across the entire class. Thus, the results for naproxen demonstrated the S or (+) isomer to be much more active in vivo, indicating a relatively slow inversion of the inactive R or (−) isomer to the active S or (+) isomer; the results for fenoprofen and ibuprofen, on the other hand, demonstrated the inactive R or (−) and the active S or (+) isomers to be approximately equally effective in vivo, indicating a rapid inversion of R or (−) isomer to S or (+) isomer. Hutt et al indicated that flurbiprofen had an S(+)/R(−) activity ratio in vivo of 878 and in vitro 2–16; the in vitro study involved antagonism of rat SRS-A on the tracheal chain of guinea pigs and the in vivo study assessed guinea pig anaphylaxis. The reference cited by Hutt et al for the flurbiprofen studies was Greig et al, *J. Med. Chem.* 18, 112–116 (1975).

Greig et al, who were associated with the Upjohn Company, one of the developers of flurbiprofen, studied the antagonism of slow reacting substance in anaphylaxis (SRS-A) and other spasmogens on the guinea pig tracheal chain by hydrotropic acids. Greig et al also studied the ability of the hydrotropic acids to protect guinea pigs against anaphylaxis. Among the substances tested were racemic flurbiprofen, (+) flurbiprofen and (−) flurbiprofen.

In the in vitro testing, the (+) isomer was found to be many times more effective than the racemate; indeed, the authors found that the (−) isomer inhibited the effect of the (+) isomer in antagonism of rat SRS-A on guinea pig trachea in vitro. In the in vivo testing, Greig et al found that flurbiprofen and its isomers were active in protecting sensitized guinea pigs against anaphylactic shock when they were challenged 4 weeks after sensitization. These results correlated well with the in vitro activity. in vivo, the (+) isomer had more than a two-fold effect over the racemate; at 80% protection, the (+) isomer was 5 to 7 times more active than the racemic mixture. The (−) isomer was the least active of the three compounds.

The Greig et al studies concerned themselves with anaphylaxis and bronchospasm; as such, they have no relevancy to analgesia or inflammation.

Nishizawa et al, also associated with Upjohn, reported in *Thrombosis Research* 3, 577–588 (1973) on flurbiprofen as a potent inhibitor of platelet aggregation in animals and man. They found that the platelet anti-aggregating effect resided in the d-isomer; the l-isomer was without anti-aggregating effect and neither counteracted nor enhanced the effect of the d-isomer. The optical antipodes were tested in rats. Anti-aggregating effects, however, do not correlate with models for analgesia or inflammation.

Kulmacz et al, *J. Biol. Chem,* 260, 12572–12578 (1985), studied the interaction of flurbiprofen with prostaglandin H synthase. They reported that 1.2±0.1 mol of S(+) flurbiprofen per mol of synthase dimer resulted in maximum inhibition of the cyclooxygenase enzyme. Racemic flurbiprofen required 2.4±0.3 mol per mol synthase dimer for full effect, and the R(−) isomer was not inhibitory, even at a ratio of 2.5/dimer. From their own studies and those of Nishizawa et al in inhibiting rat platelet aggregation, Kulmacz et al concluded that the flurbiprofen isomers follow the pattern observed for many anti-inflammatory agents, i.e., the dextrorotatory form is usually more potent pharmacologically than the levorotatory isomer. This is borne out by the teachings of Armitage et al, U.S. Pat. No. 4,501,727, dated Feb. 26, 1985. The Armitage et al patent relates to a novel light-stable N-methyl-D-glucamine salt of the dextrorotatory or (+) isomer. It teaches that flurbiprofen has anti-inflammatory, analgesic and antipyretic properties, and that the (+) enantiomer is the pharmacologically active isomer.

In summary, the current state of the art assumes that, in mammals, analogously to other 2-arylpropionic acid NSAID's, the S(+) form is the active enantiomer of flurbiprofen. However, there do not appear to be any human or other animal experiments on efficacy of the separate enantiomers in analgesic or anti-inflammatory models reported in the literature. The prior art, moreover, is conspicuously silent in respect to any sustainedly enhanced alleviation of mammalian pain utilizing whatever form of the flurbiprofen drug species.

SUMMARY OF THE INVENTION

Surprisingly, the present inventors now find that S(+) flurbiprofen free acid can be advantageously administered to mammals suffering from pain, especially humans, to not only elicit a more potent analgesic response but also to evoke such enhanced response over a longer period of time than possible by administration of the same dose of flurbiprofen in its racemic form.

In one aspect, the present invention thus provides a method of providing enhanced and sustained or prolonged analgesia in a mammal, said method comprising administering to a mammal in need of such treatment an effective analgesia enhancing and sustaining amount of S(+) flurbiprofen free acid substantially free of R(−) flurbiprofen.

In yet another aspect, the present invention provides a pharmaceutical composition of matter for use in eliciting an enhanced and sustained analgesic response in mammals, especially humans, said composition comprising an effective analgesia enhancing and sustaining unit dosage amount of S(+) flurbiprofen free acid substantially free of R(−) flurbiprofen. Typically, S(+) flurbiprofen is associated with a nontoxic pharmaceutically acceptable inert carrier or diluent therefor.

BRIEF DESCRIPTION OF THE DRAWINGS

FIG. 1 is a plot of mean Pain Intensity Difference (PID) against time in hours, in patients with postepisiotomy pain, comparing 25 mg racemic flurbiprofen (RF-25 mg), 50 mg racemic flurbiprofen (RF-50 mg), 12.5 S(+) flurbiprofen [S(+) F-12.5 mg], 25 mg S(+) flurbiprofen [S(+) F-25 mg] and placebo; and FIG. 2 is a plot of mean relief values against time in hours in the same patients and comparing the same dosage levels as in FIG. 1.

DETAILED DESCRIPTION OF THE PREFERRED EMBODIMENTS OF THE INVENTION

The term "flurbiprofen" or "racemic flurbiprofen" as used herein is intended to encompass not only (±)-2-fluoro-o-methyl-[1,1'-biphenyl]-4acetic acid itself but also any pharmaceutically acceptable salt thereof.

The term "S(+) flurbiprofen" as used herein is intended to encompass not only the preferred free acid dextrorotatory or S(+) isomer of 2-fluoro-α-methyl[1,1'-biphenyl]-4-acetic acid but also includes the pharmaceutically acceptable, analgesically effective simple metal salts thereof, e.g., Na, K and Ca. The expression "substantially free of R(−) flurbiprofen" as used in conjunction with the term "S(+) flurbiprofen" means that the S(+) flurbiprofen is sufficiently free of R(−) flurbiprofen [which is the levorotatory form or R(−) isomer of 2-fluoro-α-methyl[1,1'-biphenyl]-4-acetic acid or salt thereof] to exert the desired sustained and enhanced analgesic effect. Practically speaking, this means that the active ingredient should contain at least 90% by weight S(+) flurbiprofen and 10% or less by weight R(−) flurbiprofen. Preferably, the weight ratio of S(+) flurbiprofen to R(−) flurbiprofen is greater than or equal to 20:1, more preferably greater than 97:3. Ideally the S(+) flurbiprofen is 98, 99 or more % by weight free of R(−) flurbiprofen, i.e., the weight ratio of S to R is approximately equal to or greater than 98:2 or 99:1.

Where specific amounts of S(+) flurbiprofen are set forth below, it should be understood that, unless otherwise specified, the amounts are given in mg of the acid, not of a salt. Moreover, unless otherwise specified, for simplicity's sake the amounts given represent total flurbiprofen content, most of which is in the S(+) form. For example, "50 mg S(+) flurbiprofen" means 50 mg total flurbiprofen at least 90% of which is in the S(+) form, preferably at least 95%.

S(+) flurbiprofen, in accord with the present invention, produces the following unexpected results:

(1) the analgesic effect of flurbiprofen on the mammal is significantly better than by use of racemic flurbiprofen, at a dose one-half that of racemic flurbiprofen; and (2) a greater analgesic response is elicited particularly after the first hour than is elicited by twice as much racemic flurbiprofen.

These unexpected results can be achieved in the treatment of pain responsive to an NSAID (non-steroidal anti-inflammatory drug) and specifically pain associated with inflammation. This includes, for example, postpartum and postoperative pain, dental pain, headache pain, dysmenorrhea, pain of musculoskeletal origin and pain and discomfort associated with respiratory infections such as colds and flu.

For patients suffering from such pain, who require treatment at a particular dose of racemic flurbiprofen, the duration and extent of effective relief is clearly of paramount importance. The present inventors' discovery that S(+) flurbiprofen, when used in place of racemic ketoprofen at one-half the dosage of the racemate, substantially enhances the analgesic response, especially after the first hour, is therefore very significant. It is likewise quite unexpected. Moreover, in patients suffering from inflammatory or degenerative joint disease, e.g. rheumatoid arthritis, osteoarthritis, gout or acute musculo-skeletal disease, the duration of analgesia is extremely important; pain is an important component of these disease states and better and more lasting relief from pain is of substantial psychological benefit. The S(+) flurbiprofen will, of course, over time provide relief from other aspects of inflammatory disease as well, including, e.g. morning stiffness.

The precise amount of S(+) flurbiprofen for use in accord with the present invention will vary depending, for example, on the size and kind of the mammal and the condition for which the drug is administered. For use in humans, the analgesically effective amount of S(+) flurbiprofen will typically be from about 12.5 to 50 mg, although greater amounts (e.g. 75 mg) may be employed if needed for pain relief and if tolerated by the patient. The daily dose in humans preferably will not exceed 150 mg S(+) flurbiprofen, although greater amounts could be employed if tolerated by the patient. Preferred unit dosage compositions for use in the treatment of mild to moderate pain having an inflammatory component contain 12.5, 25 or 50 mg S(+) flurbiprofen.

While the compositions for use in the invention are preferably for oral use, they may also be formulated for and administered by other routes which are known for administering non-narcotic analgesics/nonsteroidal anti-inflammatory drugs, e.g. as suppositories or parenteral solutions, or as topical formulations such as ointments, gels, creams, lotions, solutions, impregnated bandages or other topical delivery devices, and so forth. Also, it should be noted that the preferred human dosage levels indicated above are for use in adults; pediatric compositions would contain proportionately less of the active ingredient.

The compositions for use herein are very conveniently administered to mammals by any route of administration suitable for racemic flurbiprofen, e.g. oral, rectal, topical or parenteral. Preferably S(+) flurbiprofen is formulated with any suitable nontoxic pharmaceutically acceptable inert carrier material. Such carrier materials are well known to those skilled in the art of pharmaceutical formulations. For those not skilled in the art, reference is made to the text entitled *Remington's Pharmaceutical Sciences,* 17th edition, 1985, ed. Alfonso R. Gennaro, Mack Publishing Company, Easton, Pa. 18042. In a typical preparation for oral administration, e.g. tablet, capsule or caplet, S(+) flurbiprofen in an effective analgesic amount and substantially free of R(−) flurbiprofen, is combined with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citrus pulp, carboxymethylcellulose and sodium lauryl sulfate. If desired, a conventional pharmaceutically acceptable dye can be incorporated into the dosage unit form, i.e., any of the standard FD&C dyes. Sweetening and flavoring agents and preservatives can also be included, particularly when a liquid dosage form is formulated, e.g. an elixir, suspension or syrup. Also, when the dosage form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac and/or sugar. Such compositions should preferably contain at least 0.1% of S(+) flurbiprofen; generally, S(+) flurbiprofen will be from about 2% to about 60% of the weight of the unit. Typical unit dosage forms for oral administration will preferably contain about 12.5 to 50 mg S(+) flurbiprofen, if formulated for immediate release, as is preferred. If the composition is intended for sustained release, much larger amounts of the active ingredient would of course be incorporated into an individual unit; in such case, at least 12.5, and preferably up to 50 mg of the total amount of S(+) flurbiprofen, should be formulated for immediate release so as to obtain the desired degree of enhanced and prolonged analgesia.

A typical capsule for oral administration may contain, in addition to the selected amount of S(+) flurbiprofen, the following combination of inactive ingredients/carrier materials: D&C Yellow 10, FD&C Blue 1, FD&C Yellow 6, gelatin, lactose, magnesium stearate and titanium dioxide.

Moreover, the compositions for use in obtaining enhanced and prolonged analgesia in accord with the present invention may, in addition to the selected dose of S(+) flurbiprofen, also contain other active ingredients and/or enhancing agents. Thus, for example, S(+) flurbiprofen may be combined with such ingredients and agents as have been described for combination with racemic flurbiprofen, e.g. caffeine or other xanthine derivative, a narcotic analgesic (with or without caffeine), a skeletal muscle relaxant, an antihistamine, decongestant, cough suppressant and/or expectorant. See, for example, Sunshine et al U.S. Pat. No. 4,486,436, issued Dec. 4, 1984; Sunshine et al U.S. Pat. No. 4,552,899, issued Nov. 12, 1985; Sunshine et al U.S. Pat. No. 4,567,183, issued Jan. 28, 1986; and Sunshine et al U.S. Pat. No. 4,619,934, issued Oct. 28, 1986; and Sunshine et al pending U.S. patent application Ser. No. 815,502, filed Jan. 2, 1986.

The enhanced and sustained analgesic effect obtained by use of S(+) flurbiprofen in comparison with racemic flurbiprofen can be evaluated in animal and human studies such as those described below.

Antiphenylquinone Writhing Test

This test is a standard procedure for detecting and comparing analgesic activity and generally correlates well with human efficacy.

Mice are first dosed with the medications studied. The medications used are two dose levels of S(+) flurbiprofen and two dose levels of racemic flurbiprofen. The mice are then challenged with phenyl-p-benzoquinone given intraperitoneally and observed for the characteristic stretch-writhing syndrome. Lack of writhing constitutes a positive response. The degree of analgesic protection can be calculated on the basis of suppression of writhing relative to control animals run the same day. Time response data are also obtained. Observations are made long enough post-dosing to detect differences with increasing time. The test is a modification from the methods of Sigmund et al and Blumberg et al (Sigmund, E., Cadmus, R., and Lu, G., *Proc. Soc. Exo. Biol. and Med.* 95, 729–731, 1957; Blumberg, H., et al, *Proc. Soc. Exp. Biol. and Med.* 118, 763–766, 1965).

The Inflamed Rat Paw Test: Pressure Induced Stimuli

The method of Randall-Selitto, modified according to Winter et al, is used to ascertain the escape response threshold resulting from the application of increasing pressure to the yeast inflamed left hind paw. Drug treatment is given. The medications studied are two dose levels of S(+) flurbiprofen and two dose levels of racemic flurbiprofen. A constantly increasing force is applied to the paw and the "flight reaction" is observed and recorded at several points in time (Randall, L. Q., and Selitto, J. J.: *Arch. Int. Pharmacodyn.*, II, 409–419, 1957; Winter, C. A., and Lars, F.: *J. Pharmacol. Exp. Therap.* 148, 373–379, 1965). Observations are made long enough post-dosing to detect differences with increasing time.

To establish the efficacy in humans of S(+) flurbiprofen relative to racemic flurbiprofen, a study was performed in an appropriate pain model. Thus, dosages of 25 mg and 50 mg of racemic flurbiprofen were compared with dosages of 12.5 mg and 25 mg of S(+) flurbiprofen, in patients with moderate to severe postepisiotomy pain requiring an oral analgesic/anti-inflammatory agent. A randomized double-blind single dose clinical trial comparing racemic flurbiprofen (RF 25 mg and 50 mg, S(+) flurbiprofen [S(+)F 12.5 mg and 25 mg) and placebo was conducted in 149 patients. An observer interviewed patients as to their level of pain intensity at baseline, ½ hour, 1 hour and hourly thereafter, until six hours post-dosing. At the same interview times, patients were asked to estimate their degree of RELIEF. Pain intensity levels were subtracted from the baseline pain intensity level to form the variables, Pain Intensity Difference (PID). SPID is the sum of the PID scores weighted by the length of the time intervals between observations and is an estimate of the area under the time effect curve. Analogously, the variable TOTAL is the weighted sum of RELIEF variables.

FIG. 1 and TABLE 1 below show the time-effect curve for the variable PID's, while FIG. 2 and TABLE 2 show the time-effect curve for the mean relief variables.

TABLE 1

| | PID | | | | | |
|---|---|---|---|---|---|---|
| | R F-25 mg | R F-50 mg | S(+) F-12.5 mg | S(+) F-25 mg | PLACEBO | HOURS |
| 1 | 0 | 0 | 0 | 0 | 0 | 0 |
| 2 | 0.567 | 0.581 | 0.655 | 0.484 | 0.536 | .5 |
| 3 | 0.833 | 0.935 | 1.000 | 0.871 | 0.750 | 1.0 |
| 4 | 1.033 | 1.129 | 1.517 | 1.290 | 0.750 | 2.0 |
| 5 | 1.267 | 1.226 | 1.724 | 1.452 | 0.857 | 3.0 |
| 6 | 1.333 | 1.419 | 1.966 | 1.710 | 0.857 | 4.0 |
| 7 | 1.433 | 1.613 | 1.966 | 1.839 | 0.821 | 5.0 |
| 8 | 1.433 | 1.645 | 1.966 | 1.871 | 0.857 | 6.0 |

TABLE 2

| | RELIEF | | | | | |
|---|---|---|---|---|---|---|
| | R F-25 mg | R F-50 mg | S(+) F-12.5 mg | S(+) F-25 mg | PLACEBO | HOURS |
| 1 | 0 | 0 | 0 | 0 | 0 | 0 |
| 2 | 1.000 | 0.871 | 0.931 | 0.806 | 0.821 | .5 |
| 3 | 1.400 | 1.387 | 1.621 | 1.258 | 1.036 | 1.0 |
| 4 | 1.800 | 1.806 | 2.379 | 2.032 | 1.107 | 2.0 |
| 5 | 2.000 | 2.000 | 2.690 | 2.226 | 1.321 | 3.0 |
| 6 | 2.200 | 2.258 | 2.931 | 2.548 | 1.393 | 4.0 |
| 7 | 2.300 | 2.516 | 2.931 | 2.677 | 1.357 | 5.0 |

TABLE 2-continued

| | R F-25 mg | R F-50 mg | S(+) F-12.5 mg | S(+) F-25 mg | PLACEBO | HOURS |
|---|---|---|---|---|---|---|
| 8 | 2.300 | 2.548 | 3.000 | 2.742 | 1.429 | 6.0 |

It can be seen that the treatments were virtually indistinguishable in the first hour; however, by the second hour and thereafter, both of the doses of the S(+) enantiomer of flurbiprofen had higher mean scores than both of the dosages of racemic flurbiprofen. The average of the responses to the two doses of S(+)F was statistically significantly superior ($p \leq 0.05$) to the average of the responses to the two doses of RF for the variables PID at hours 2, 3, 4, 5 and 6 and RELIEF at hours 2, 3, 4, and 6, as well as SPID and TOTAL.

There were no significant differences between the two doses of S(+)F and there were no significant differences between the two doses of RF, although for S(+)F the higher dose was not as effective on the average as the lower dose. This suggests that the two dose levels are too close together to distinguish a statistically significant dose response for either S(+)F or RF for the sample size of patients used in this study.

In conclusion, the average of the pain scores of the two doses of the S(+) isomer was significantly better than the average of the pain scores for the two doses of the racemate. The efficacy of S(+) flurbiprofen was particularly notable after the first hour. If the S(+) isomer were the active isomer, as taught by the art, and the R(−) isomer were not converted in vivo to the active enantiomer, one would expect the results of this study to be equal because the racemate was used at twice the dose of the S(+) isomer. [If conversion of the R(−) to the S(+) isomer were to occur, results from the racemate would be expected to be superior.] The finding that S(+) flurbiprofen is a statistically superior analgesic to racemic flurbiprofen at half the dose of the racemate is therefore quite surprising and unexpected in view of the prior art.

S(+) flurbiprofen for use in the method and compositions of the present invention can be prepared by a variety of methods, such as by resolution of racemic flurbiprofen.

Maitre et al, *J. Chromatoor.* 299, 397–403 (1984) have resolved racemic flurbiprofen and a number of other arylpropionic acids by high-performance liquid chromatographic (HPLC) separation. The diastereoisomeric derivatives of the racemic acids with S(−) 1-phenylethylamine were synthesized and then separated by the HPLC method. The pure amides could then be used to regenerate the corresponding acids, now in optically pure form, as is well-known.

HPLC methods other than Maitre et al's for resolving enantiomers of NSAID's such as ibuprofen, ketoprofen and fenoprofen, and likely adaptable to resolution of flurbiprofen, include the method of Doyle et al, *Pharm. Technol.* 9(2), 28–32 (1985), which utilizes conversion of the racemate to its amide derivatives for effective resolution; that of Wainer et al, *J. Chromatoor.* 284(1), 117–124 (1984), which utilizes conversion of the drug to 1-naphthalenemethylamide derivatives; and that of Sallustio et al, *J. Chromatogr.*, 374, 329–337 (1986), which employs conversion of the drug to the R and S derivatives of R-2-phenylethylamine.

A method for derivatizing flurbiprofen and other nonsteroidal anti-inflammatory drugs with optically active amphetamine (α-methylbenzeneethanamide) has been described by Singh et al, *J. Chromatogr. Biomed Appln.* 378, 125–135 (1986). Those authors also provide a summary of the usual methods for resolving enantiomers, i.e. (1) by direct separation on chiral HPLC or GC (gas chromatographic) columns, or (2) by diastereoisomer formation, by reaction with an optically pure resolving agent, followed by chromatographic separation on an optically inactive column. Singh et al's method is a new version of the second approach, using optically active amphetamine as the resolving agent, followed by separation of the diastereoisomers by capillary gas chromatography with nitrogen-phosphorus detection. (The acid, now in optically pure form, could of course then be regenerated from the salt as is well-known.) The usual method in the art utilizes optically active α-methylbenzylamine and involves preparation of the diastereoisomeric NSAID-α-methylbenzylamide directly by means of a coupling agent (e.g. 1,1'-carbonyldiimidazole) or via the NSAID acid chloride (prepared with thionyl chloride). An example of the first approach has been provided by Hermansson et al, *Journal of Liquid Chromatography*, 9 (2 & 3), 621–639 (1986); those authors describe direct liquid chromatographic resolution of such acidic drugs as ibuprofen, ketoprofen, naproxen and 2-phenoxypropionic acid, using a chiral $\alpha_1$-acid glycoprotein column (Enantiopak ®).

More generally speaking, the S(+) isomer can be separated from racemic flurbiprofen by preparing a salt of flurbiprofen with an alkaloid or similar resolving agent such as cinchonidine, then separating the products by fractional crystallization from a solvent in which the dextrorotatory isomer is least soluble. The d-salt can then be acid cleaved to yield S(+) flurbiprofen. Compare, for example, Alvarez U.S. Pat. No. 3,637,767, issued Jan. 25, 1972, which relates to resolution of naproxen and related compounds; and Kaiser et al, *J. Pharm. Sci.* 65(2). 269–273 (1976), which relates to resolution of ibuprofen.

While S(+) flurbiprofen may be conveniently obtained by resolution of racemic flurbiprofen, it may also be possible to utilize a chemical or microbiological synthetic process which will provide the S(+) enantiomer directly. One such chemical process is provided by Schloemer U.S. Pat. No. 4,542,237, which describes a process for preparing α-arylalkanoic acids utilizing novel α-hydroxy alkyl aryl ketals as intermediates. As taught in column 9 of the Schloemer patent, the process is advantageous in that the α-hydroxy ketal can be resolved by well-known methods and the optically active α-hydroxy ketal thus obtained can then be used in the subject process to ultimately afford the desired acid in optically pure form.

Alternatively, a microbiological process such as that described in SHELL INTERNATIONALE RESEARCH MAATSCHAPPIJ B.V.'s European Patent Appln. No. 86 200987.5, published under No. 0 205215 on Dec. 17, 1986, may be employed. According to the European application, a pharmaceutically active compound of the type

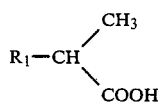

or a pharmaceutically active salt or ester thereof, which most preferably is naproxen or ibuprofen but which may be flurbiprofen or various other NSAIDs, is prepared in stereospecific form by subjecting a compound of the formula

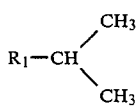

to the action of an appropriate microorganism. The desired acid is obtained having at least 70% by weight in the S-configuration. Preferably, a microorganism is selected such that the acid which is formed is at least 90% by weight in the S-configuration. Use of this method has afforded naproxen with enantiomeric distributions of 98.9% S and 1.1% R in one instance, and distributions of 99.5% S and 0.5% R in another. Processes of this type may be utilized to prepare S(+) flurbiprofen for use in the present invention if the S(+) isomer can be obtained in sufficient purity [ideally, at least 90% by weight S(+) isomer.]

When S(+) flurbiprofen is to be employed in the form of a pharmaceutically acceptable, analgesically active simple metal salt thereof, such salt may be conveniently prepared by direct salification of S(+) flurbiprofen by known methods. See, for example, deVincentiis U.S. Pat. No. 4,440,787, which describes salts of (2',4'-difluoro-4-biphenyl)oxypropionic acid with metallic ions, such as sodium, potassium, magnesium and calcium. Nonetheless, the free acid form is the preferred. Compare also Armitage et al U.S. Pat. No. 4,501,727, issued Feb. 26, 1985, which describes the N-methyl-D-glucamine salt of flurbiprofen. Such a salt may not only be used in oral or rectal compositions, but, because it is highly soluble in water, it may be used in the preparation of aqueous solutions of S(+) flurbiprofen salt for parenteral injection, as indicated by Armitage et al.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be within the full range of equivalence of the following claims.

What is claimed is:

1. The method of eliciting a sustained, enhanced analgesic response in a human mammal suffering from pain and in need of such treatment, comprising administering to such organism a unit dosage sustainedly enhancing, analgesically effective amount of the S(+) flurbiprofen enantiomer, and said enentiomer being substantially free of its R(−) flurbiprofen antipode.

2. A method according to claim 1, wherein the weight ratio of S(+) flurbiprofen to R(−) flurbiprofen is greater than 9:1.

3. A method according to claim 2, wherein the weight ratio of S(+) flurbiprofen to R(−) flurbiprofen is greater than or approximately equal to 20:1.

4. A method according to claim 3, wherein the weight ratio of S(+) flurbiprofen to R(−) flurbiprofen is greater than 97:3.

5. A method according to claim 4, wherein the weight ratio of S(+) flurbiprofen to R(−) flurbiprofen is approximately equal to or greater than 98:2.

6. A method according to claim 1, comprising administering to such organism from about 12.5 to about 75 mg S(+) flurbiprofen.

7. A method according to claim 1, comprising administering to such organism from about 12.5 to about 50 mg S(+) flurbiprofen.

8. A method according to claim 1, comprising administering to such organism from about 12.5 to about 25 mg S(+) flurbiprofen.

9. A method according to claim 2, comprising administering to such organism from about 12.5 to about 75 mg S(+) flurbiprofen.

10. A method according to claim 2, comprising administering to such organism from about 12.5 to about 50 mg S(+) flurbiprofen.

11. A method according to claim 2, comprising administering to such organism from about 12.5 to about 25 mg S(+) flurbiprofen.

12. A method according to claim 3, comprising administering to such organism from about 12.5 to about 75 mg S(+) flurbiprofen.

13. A method according to claim 3, comprising administering to such organism from about 12.5 to about 50 mg S(+) flurbiprofen.

14. A method according to claim 3, comprising administering to such organism from about 12.5 to about 25 mg S(+) flurbiprofen.

15. A method according to claim 4, comprising administering to such organism from about 12.5 to about 75 mg S(+) flurbiprofen.

16. A method according to claim 4, comprising administering to such organism from about 12.5 to about 50 mg S(+) flurbiprofen.

17. A method according to claim 4, comprising administering to such organism from about 12.5 to about 25 mg S(+) flurbiprofen.

18. A method according to claim 5, comprising administering to such organism from about 12.5 to about 75 mg S(+) flurbiprofen.

19. A method according to claim 5, comprising administering to such organism from about 12.5 to about 50 mg S(+) flurbiprofen.

20. A method according to claim 5, comprising administering to such organism from about 12.5 to about 25 mg S(+) flurbiprofen.

21. A method according to claim 1, wherein such organism is suffering from postoperative pain.

22. A method according to claim 1, wherein such organism is suffering from postpartum pain.

23. A method according to claim 1, wherein such organism is suffering from dental pain.

24. A method according to claim 1, wherein such organism is suffering from dysmenorrhea.

25. A method according to claim 1, wherein such organism is suffering from headache pain.

26. A method according to claim 1, wherein such organism is suffering from musculoskeletal pain.

27. A method according to claim 1, wherein such organism is suffering from pain or discomfort associated with a respiratory infection.

28. A method according to claim 1, wherein such organism is suffering from pain or discomfort associated with a cold or flu.

29. A method according to claim 1, wherein such organism is suffering from pain associated with inflammatory or degenerative joint disease.

30. A method according to claim 1, wherein such organism is suffering from pain associated with rheumatoid arthritis.

31. A method according to claim 1, wherein such organism is suffering from pain associated with osteoarthritis.

32. A method according to claim 1, wherein such organism is suffering from pain associated with gout.

33. A method according to claim 1, wherein such organism is suffering from pain associated with morning stiffness.

34. A method according to claim 1, wherein the S(+) flurbiprofen is orally administered to such organism.

35. A method according to claim 1, wherein the S(+) flurbiprofen is rectally administered to such organism.

36. A method according to claim 1, wherein the S(+) flurbiprofen is topically administered to such organism.

37. A pharmaceutical composition of matter adapted to elicit a sustained, enhanced analgesic response in a mammalian organism in need of such treatment, said composition comprising a solid-state unit dosage sustainedly enhancing, analgesically effective amount of the S(+) flurbiprofen enantiomer, said enantiomer being substantially free of its R(−) antipode, and a nontoxic pharmaceutically acceptable carrier or diluent therefor.

38. The pharmaceutical composition of matter according to claim 37, adapted for oral administration.

39. The pharmaceutical composition of matter according to claim 38, formulated as a tablet, caplet, pill or capsule.

40. The pharmaceutical composition of matter according to claim 37, adapted for rectal administration.

41. The pharmaceutical composition of matter according to claim 40, formulated as a suppository.

* * * * *

UNITED STATES PATENT AND TRADEMARK OFFICE
CERTIFICATE OF CORRECTION

PATENT NO. : 4,927,854
DATED : May 22, 1990
INVENTOR(S) : Abraham Sunshine, et al It is certified that error appears in the above-indentified patent and that said Letters Patent is hereby corrected as shown below:

On the Title Page, Item [75]:

Add --John A. Rees-- as a coinventor.

Signed and Sealed this

Nineteenth Day of April, 1994

*Attest:*

BRUCE LEHMAN

*Attesting Officer*     *Commissioner of Patents and Trademarks*